(12) United States Patent
Chang et al.

(10) Patent No.: US 8,420,316 B2
(45) Date of Patent: Apr. 16, 2013

(54) METHOD FOR COLUMBIDAE GENDER IDENTIFICATION, NUCLEOTIDE SEQUENCE FOR COLUMBIDAE GENDER AND NUCLEOTIDE PRIMER PAIR FOR COLUMBIDAE GENDER

(75) Inventors: Hsueh-Wei Chang, Kaohsiung (TW); Chien-Chung Cheng, Taipei (TW); Ying-Fang Su, Kaohsiung (TW); Yu-Chen Hung, Tainan County (TW)

(73) Assignee: Kaohsiung Medical University, Kaohsiung (TW)

( * ) Notice: Subject to any disclaimer, the term of this patent is extended or adjusted under 35 U.S.C. 154(b) by 272 days.

(21) Appl. No.: 12/854,864

(22) Filed: Aug. 11, 2010

(65) Prior Publication Data

US 2011/0244463 A1    Oct. 6, 2011

(30) Foreign Application Priority Data

Mar. 31, 2010 (TW) ................. 99109810 A

(51) Int. Cl.
*C12Q 1/68* (2006.01)
(52) U.S. Cl.
USPC .......................................... 435/6.1
(58) Field of Classification Search ........................ None
See application file for complete search history.

(56) References Cited

PUBLICATIONS

Wu et al. (Theriogenology. Jan. 15, 2007;67(2):328-33. Epub Sep. 11, 2006).*
Chang et al. (BMC Biotechnol. Feb. 12, 2008;8:12).*
Griffiths et al., "A DNA test to sex most birds", Molecular Ecology, 7:1071-1075, 1998.
Wu et al., "A novel sex-specific DNA marker in Columbidae birds", Theriogenology, 67:328-333, 2007.
Chang et al., "An improved PCR method for gender identification of eagles", Molecular and Cellular Probes, 22:184-188, 2008.
Reddy et al., "A rapid, non-invasive, PCR-based method for identification of sex of the endangered Old World vultures (white-backed and long-billed vultures)—Implications for captive breeding programmes", Current Science, vol. 92, No. 5, 659-662, 2007.
Huang et al., "AFLP fingerprinting for paternity testing in ducks", British Poultry Science, vol. 48, No. 3, 323-330, 2007.
Sacchi et al., "A non-invasive test for sex identification in Short-toed Eagle (*Circaetus gallicus*)", Molecular and Cellular Probes, 18:193-196, 2004.
Fridolfsson et al., "A simple and universal method for molecular sexing of non-ratite birds", Journal of Avian Biology, 30:116-121, 1999.

* cited by examiner

*Primary Examiner* — Christopher M. Babic
(74) *Attorney, Agent, or Firm* — Pai Patent & Trademark Law Firm; Chao-Chang David Pai

(57) ABSTRACT

The invention provides a method for Columbidae gender identification including: providing a DNA sample of a bird belonging to the Columbidae family; performing a polymerase chain reaction to the DNA sample with a first primer pair of a first primer designed within the region of the SEQ ID. NO.: 9 or a complementary sequence thereof and a P2 primer (SEQ ID. NO: 1) or a complementary sequence thereof, and a second primer pair of a second primer designed within the region of the SEQ ID NO.: 10 or a complementary sequence thereof and a P2 primer (SEQ ID. NO: 1) or a complementary sequence thereof; and determining gender by performing a melting curve analysis to a product from the polymerase chain reaction, wherein the result showing two peaks indicate a female gender and showing one peak indicate a male gender.

16 Claims, 10 Drawing Sheets

*S. tranquebarica*

```
             P2 primer
             TCTGCATGCTAAATCCTT
C.livia-Z     TCTGCATGCTAAATCCTTAATATTTCTCGAGGAATGGTTCGTGGTCTTCCACGTTTT
C.pulchricollis-Z TCTGCATGCTAAATCCTTAATATTTCTCGAGGAATGGTTCGTGGTCTTCCACGTTTT
S.tranquebarica-Z TCTGCATGCTAAATCCTTAATATTTCTCGAGGAATGGTTCGTGGTCTTCCACGTTTT
C.livia-W     TCTGCATGCTAAATCCTTAATATTTCTCGAGGAATGGTTCGTGGTCTTCCACGTTTT
C.pulchricollis-W TCTGCATGCTAAATCCTTAATATTTCTCGAGGAATAGTTCGTGGTCGTCCACGTTTT
S.tranquebarica-W TCTGCATGCTAAATCCTTATGCATTTCTCGAGGAATAGTTCGTGGTCGTCCACGTTTT
              **************************        ********  ********

ZW-common
C.livia-Z     TTTGGCCGTTTTCTTTCTGATATGGAGTCACTATCAGATCCAGAGGTATCTTCTGCTCCTA
C.pulchricollis-Z TTTGGCCGTTTTCTTTCTGATATGGAGTCACTATCAGATCCAGAGGTATCTTCTGCTCCTA
S.tranquebarica-Z TTTGGCCGTTTTCTTTCTGATATGGAGTCACTATCAGATCCAGAGGTATCTTCTGCTCCTA
C.livia-W     TTTGGTCGTTTTCTTTCTGACATGGAGTCACTATCAGATCCAGAAGTATCTTCTGCTTCTA
C.pulchricollis-W TTTGGTCGTTTTCTTTCTGAGATGGAGTCACTATCAGATCCAGAAGTATCTTCTGCTTCTA
S.tranquebarica-W TTTGGTCGTTTTCTTTCTGAGATGGAGTCACTATCAGATCCAGAAGTATCTTCTGCTTCTA
              ***** ************** ***********************  *********  ***
```

```
C.livia-Z          CTGGGCCTTCCTTCCATTAAAGCTGATCTGGAATTCAGAATAAGTAGTTCAAAG
C.pulchricollis-Z  CTGGGCCTTCCTTCCATTAAAGCTGATCTGGAATTCAGAATAAGTAGTTCAAAG
S.tranquebarica-Z  CTGGGCCTTCCTTCCATTAAAGCTGATCTGGAATTCAGAATAAGTAGTTCAAAG
C.livia-W          CTGCATTTCCCTTCCATTAAAGCTGATCTGGAATTCAGATTAAGTAGTTCAAAG
C.pulchricollis-W  CTGCATTTCCCTTCCATTAAAGCTGATCTGGAATTCAGATTAAGTAGTTCAAAG
S.tranquebarica-W  CTGCATTTCCGTTCCATTAAAGCTGATCTGGAATTCAGATTAAGTAGTTCAAAG
                   *** * ***** ************************* *** *************

C.livia-Z          CTATGCGATTGACAAACACAGGTCAAGTTTGCCTAACCTGTCAAAATACGTGTTCAGA
C.pulchricollis-Z  CTACGCGATTGACAAACACAGGTCAAGTTTGCCTAACCTGTCAAAATACGTGTTCAGA
S.tranquebarica-Z  CTACGCGATTGACAAACACAGGTCAAGTTTGCCTAACCTGTCAAAATACGTGTTCAGA
C.livia-W          CTATGTGACTAAAACATTTTAATAATGTGCTATCTAGCCTGTCAAAATATGTGTTCAGA
C.pulchricollis-W  ATATGTGACTAAAACATTTTAATAATGTGCTATCTAGCCTGTCAAAA----------
S.tranquebarica-W  CTATGTGACTAAAACATTTTAATAATGTGCTATCTAGCCTGTCAAAA----------
                   ** * ***  *  *   *     *** *** * *** ***********

C.livia-Z          AAACGGAAAAGTAC----------AAGCCAAAA--CAACAGTAA----CAACAAACCCAACAATCCCAACAACAAACTAAACCAAC
C.pulchricollis-Z  AAACGGAAAAGTAC----------AAGCCAAAA--CAACAGTAA----CAACAAACCCAACAATCCCAACAACAAACAAATTAAACCAAC
S.tranquebarica-Z  AAACGGAAAAGTAC----------AAGCCAAAA--CAACAGTAA----CAACAAACCCAACAATCCCAACAACAAACTAAACCAAC
C.livia-W          GGGTGAAAAGTAC----AAGCCAAAAA-CAACAGTAA----CCCCAACAAACCCAAC
C.pulchricollis-W  GGGTGAAAAGTAC----AAGCCAAAA---CAACAGTAA--TGAAAAAAACAAAGAAAC
S.tranquebarica-W  GGGTGAAAAGTAC----AAGCCAAAA---CAACAGTAA--TGAAAAAAACAAACAAAC
                   *  * ********      *****     ********      *** *   *  ***
                   └─1─┘            W-specific
```

FIG. 2B

```
C. livia-Z          AGCAACACAAAAGCACAAGTCAATCAGAACCAAGACACACCTGTTTGCACAGTTCCTCATCCTTGGGAG
C. pulchricollis-Z  AGCAACACAAAAGCACAAGTCAATCAGAACCAAGAGACACCTGTTTGCACAGTTCCTCATCCTTGGGAG
S. tranquebarica-Z  AGCAACACAAAAGCACAAGTCAATCAGAACCAAGACACACCTGTTTGCACAGTTCCTCATCCTTGGGAG
C. livia-W          A-CAACAACAAGAGAAGTTAGTTGGTCAAAACCCAGAGATACCTGTTTGCACAGTTCCTCATCCTTGGGAG
C. pulchricollis-W  A-CAACAACAAGAGAAGTTAGTTGGTCAAAACCCAGAGATACCTGTTTGCACAATTTCTCATCCTTGGGAG
S. tranquebarica-W  A-CAACAACAAGAGAAGTTAGTTGGTCAAAACCCAAAGATACCTGTTTGCACAGTTCCTCATCCTTGGGAG
                    * *****  **     ***    * *** **  *  *  ************** *  ***************
                                                                 CARTTYCTCATCCTTGGGAG
                                                                 P8 primer[anti-sense]
```

FIG. 2C

SEQUENCE LISTING

```
<160> NUMBER OF SEQ ID NOS: 13

<210> SEQ ID NO 1
<211> LENGTH: 20
<212> TYPE: DNA
<213> ORGANISM: Artificial Sequence
<220> FEATURE:
<223> OTHER INFORMATION: P2 Primer (forward primer)

<400> SEQUENCE: 1
tctgcatcgc taaatccttt                                              20

<210> SEQ ID NO 2
<211> LENGTH: 20
<212> TYPE: DNA
<213> ORGANISM: Artificial Sequence
<220> FEATURE:
<223> OTHER INFORMATION: P8 Primer (reverse primer)

<400> SEQUENCE: 2
ctcccaagga tgagraaytg                                              20

<210> SEQ ID NO 3
<211> LENGTH: 370
<212> TYPE: DNA
<213> ORGANISM: Columba livia

<400> SEQUENCE: 3
tctgcatcgc taaatccttt aatatttct cgaggaatgg ttcgtggtct tccacgtttt     60
tttggccgtt ttctttctga tatggagtca ctatcagatc cagagtatct tctgctccta   120
ctgcgccttc cttcacttcc attaaagctg atctggaatt tcagaataag tagttcaaag   180
ctatgcgatt gacaaacaca ggtcaagttt tgcctaacct gtcaaaaata cgtgttcaga   240
aaacggaaaa aaccctaaaa aaacaaaacc caacaacaat ccccaacaaa ctaaaccaac   300
agcaacacaa aagcacaagt caatcagaac caagacacac ctgttttgca cagttcctca   360
tccttgggag                                                         370
```

<210> SEQ ID NO 4
<211> LENGTH: 350
<212> TYPE: DNA
<213> ORGANISM: Columba livia

<400> SEQUENCE: 4

```
tctgcatcgc taaatccttt aatattttct cgaggaatag ttcgtggtcg tccacgtttt      60
tttggtcgtt ttctttctga catggagtca ctatcagatc cagaatatct tctgcttcta     120
ctgcatttcc cttcacttcc attaaagctg atctggaatt tcagattaag tagttcaaag     180
ctatgtgact aaaacatttt aataatgtgc tatctagcct gtcaaaaatg ggggtgaaa      240
agtacaagcc aaaaacaaca gtaatgaaaa acaaagaaa cacaacaaca agaagttagt     300
tggtcaaaac ccagagatac ctgttttgca cagttcctca tccttgggag                350
```

<210> SEQ ID NO 5
<211> LENGTH: 370
<212> TYPE: DNA
<213> ORGANISM: Columba pulchricollis

<400> SEQUENCE: 5

```
tctgcatcgc taaatccttt aatattttct cgaggaatgg ttcgtggtct tccacgtttt      60
tttggccgtt ttctttctga tatggagtca ctatcagatc cagagtatct tctgctccta     120
ctgcgccttc cttcacttcc attaaagctg atctggaatt tcagaataag tagttcaaag     180
ctacgcgatt gacaaacaca ggtcaagttt tgcctaacct gtcaaaaata cgtgttcaga     240
aaacggaaaa aaccctaaaa aaccaaaacc caacaacaat ccccaacaaa ttaaaccaac     300
agcaacacaa aagcacaagt caatcagaac caagagacac ctgttttgca cagttcctca    360
tccttgggag                                                             370
```

<210> SEQ ID NO 6
<211> LENGTH: 349
<212> TYPE: DNA
<213> ORGANISM: Columba pulchricollis

<400> SEQUENCE: 6

```
tctgcatcgc taaatccttt aatattttct cgaggaatag ttcgtggtcg tccacgtttt      60
tttggtcgtt ttctttctga gatggagtca ctatcagatc cagaatatct tctgcttcta     120
ctgcatttcc cttcgcttcc attaaagctg atctggaatt tcagattaag tagttcaaag     180
atatgtgact aaaacatttt aataatgtgc tatctagcct gtcaaaaatg ggggtgaaa      240
agtacaagcc aaaacaacag taatgaaaaa acaaacaaac aacaacaa gaagttagtt      300
ggtcaaaacc cagagatacc tgttttgcac aatttctcat ccttgggag                  349
```

<210> SEQ ID NO 7
<211> LENGTH: 367
<212> TYPE: DNA
<213> ORGANISM: Streptopelia tranquebarica

<400> SEQUENCE: 7

```
tctgcatcgc taaatccttt aatattttct cgaggaatgg ttcgtggtct tccacgtttt      60
tttggccgtt ttctttctga tatggagtca ctatcagatc cagagtatct tctgctccta     120
ctgcgccttc cttcacttcc attaaagctg atctggaatt tcagaataag tagttcaaag     180
ctacgcgatt gacaaacaca ggtcaagttt tgcctaacct gtcaaaaata tgtgttcaga     240
aaacggaaaa aaactaaaa aaacaaaacc caacaacccc caacaaacta aaccaacagc     300
```

```
aacacaaaag cacaagtcaa tcagaaccaa gagacacctg ttttgcacag tttctcatcc    360
ttgggag                                                              367

<210> SEQ ID NO 8
<211> LENGTH: 349
<212> TYPE: DNA
<213> ORGANISM: Streptopelia tranquebarica

<400> SEQUENCE: 8
tctgcatcgc taaatccttt atgcatttct cgaggaatag ttcgtggtcg tccacgtttt    60
tttggtcgtt ttctttctga gatggagtca ctatcagatc cagaatatct tctgcttcta   120
ctgcatttcc cttcgcttcc attaaagctg atctggaatt tcagattaag tagttcaaag   180
ctatgtgact aaaacatttt aataatgtgc tatctagcct gtcaaaaatg gggggtgaaa   240
agtacaagcc aaaacaacag taatgaaaaa acaaacaaac acaacaacaa gaagttagtt   300
ggtcaaaacc caaagatacc tgttttgcac agttcctcat ccttgggag              349

<210> SEQ ID NO 9
<211> LENGTH: 38
<212> TYPE: DNA
<213> ORGANISM: Artificial Sequence
<220> FEATURE:
<223> OTHER INFORMATION: CHD-W specific region or primer for CHD-W
      specific region

<400> SEQUENCE: 9 tgggggtgtga aaagtacaag ccaaaaacaa cagtaatg                           38

<210> SEQ ID NO 10
<211> LENGTH: 51
<212> TYPE: DNA
<213> ORGANISM: Artificial Sequence
<220> FEATURE:
<223> OTHER INFORMATION: CHD-ZW common region or primer for CHD-ZW
      common region

<400> SEQUENCE: 10
cgttttcttt ctgabatgga gtcactatca gatccagarg tatcttctgc t            51

<210> SEQ ID NO 11
<211> LENGTH: 20
<212> TYPE: DNA
<213> ORGANISM: Artificial Sequence
<220> FEATURE:
<223> OTHER INFORMATION: Primer for CHD-W specific region

<400> SEQUENCE: 11
gggtgaaaag tacaagccaa                                                20

<210> SEQ ID NO 12
<211> LENGTH: 23
<212> TYPE: DNA
<213> ORGANISM: Artificial Sequence
<220> FEATURE:
<223> OTHER INFORMATION: Primer for CHD-ZW common region

<400> SEQUENCE: 12
atggagtcac tatcagatcc aga                                            23

<210> SEQ ID NO 13
<211> LENGTH: 20
<212> TYPE: DNA
<213> ORGANISM: Artificial Sequence
```

```
<220> FEATURE:
<223> OTHER INFORMATION: P8 Primer (anti-sense)

<400> SEQUENCE: 13
carttyctca tccttgggag                                                  20
```

METHOD FOR COLUMBIDAE GENDER IDENTIFICATION, NUCLEOTIDE SEQUENCE FOR COLUMBIDAE GENDER AND NUCLEOTIDE PRIMER PAIR FOR COLUMBIDAE GENDER

CROSS REFERENCE TO RELATED APPLICATIONS

This Application claims priority of Taiwan Patent Application No. 099109810, filed on Mar. 31, 2010, the entirety of which is incorporated by reference herein.

BACKGROUND OF THE INVENTION

1. Field of the Invention

The present invention relates to bird gender identification, and in particular relates to Columbidae gender molecular identification.

2. Description of the Related Art

Gender identification is especially important to monitor the population size in areas that have decreased population trends. The sex ratio is an important factor in breeding birds, monitoring population growth, and detecting global changes in relationships. However, determining the sex of a bird belonging to the Columbidae family is difficult because most are monomorphic.

Traditionally, molecular gender identification of birds is based on the differences in length of intron between the chromo-helicase-DNA binding protein (CHD)-Z and CHD-W genes amplified by the Griffiths P2/P8 primer set (Griffiths R, Double M C, Orr K, Dawson R J. (1998) A DNA test to sex most birds. Molecular Ecololgy 7:1071-5), i.e., males contain a single CHD-Z band (ZZ) and females contain two bands (CHD-Z and CHD-W; ZW), after electrophoresis. Currently, other methods such as re-designed non-P2/P8 primers for polymerase chain reaction (Fridolfsson, A. and Ellegren, H. (1999) A simple and universal method for molecular sexing of non-ratite birds. Journal of Avian Biology, 30, 116-121.; Chang, H. W., Chou, T. C., Gu, D. L., Cheng, C. A., Chang, C. C., Yao, C. T., Chuang, L. Y., Wen, C. H., Chou, Y. C., Tan, K. Y. et al. (2008) An improved polymerase chain reaction method for gender identification of eagles. Molecular and cellular probes, 22, 184-188.), polymerase chain reaction-RFLP (Sacchi, P., Soglia, D., Maione, S., Meneguz, G., Campora, M. and Rasero, R. (2004) A non-invasive test for sex identification in short-toed Eagle (*Circaetus gallicus*). Molecular and cellular probes, 18, 193-196.; Reddy, A., Prakash, V. and Shivaji, S. (2007) A rapid, non-invasive, polymerase chain reaction-based method for identification of sex of the endangered Old World vultures (white-backed and long-billed vultures)—Implications for captive breeding programmes. Current Science 2007; 92:659-62), RAPD-polymerase chain reaction (Wu, C. P., Horng, Y. M., Wang, R. T., Yang, K. T. and Huang, M. C. (2007) A novel sex-specific DNA marker in Columbidae birds. Theriogenology, 67, 328-333.) and AFLP-polymerase chain reaction (Huang, C. W., Cheng, Y. S., Rouvier, R., Yang, K. T., Wu, C. P. and Huang, M. C. (2007) AFLP fingerprinting for paternity testing in ducks. Br Poult Sci, 48, 323-330.) have been developed for the gender identification of birds. However, all require the gel electrophoresis step after the polymerase chain reaction and are not robust for gender identification of birds in a high-throughput format.

Alternatively, melting curve analysis is capable of simultaneously measuring the melting temperature (Tm) for many polymerase chain reaction amplicons. The melting curve analysis does not require the electrophoresis step; thereby saving time and having high-throughput. Melting curve analysis is widely used in many fields such as for the detection of methylation, SNP genotyping and mutation, genus identification of microbials, quantification of chromosome conformation capture. However, melting curve analysis is seldom applied in the gender identification of birds.

For melting curve analysis, different Tm values for the specific polymerase chain reaction amplicons are analogous to the different shift mobilities for the corresponding electrophoretic bands. Amplicons with different lengths have different melting temperatures (Tm), ie. the longer the length is, the greater the Tm value is, and the shorter the length is, the lower the Tm value is. Therefore, it is possible that the gender of some Columbidae species may be identified using melting curve analysis based on the different Tm values of their CHD-Z and CHD-W amplicons. Although melting curve analysis may be used to determine Tm values for CHD-Z and CHD-W amplicons, their differences in length may vary from species to species. Accordingly, melting curve analysis for species wherein the difference in length of intron for CHD-Z and CHD-W amplicons is small, which results in a small Tm value difference therebetween, is not applicable as the degree of resolution for real-time polymerase chain reaction machines may be insufficient.

Recently, for gender identification of three species belonging to the Columbidae family, a female-specific primer generated from an RAPD method has been disclosed (Wu, C. P., Horng, Y. M., Wang, R. T., Yang, K. T. and Huang, M. C. (2007) A novel sex-specific DNA marker in Columbidae birds. Theriogenology, 67, 328-333.). The polymerase chain reaction product for the lengths of 777-, 778-, and 770-bp, for three species belonging to the Columbidae family such as *Streptopelia orientals, Streptopelia chinensis* and *Columba livia*, have been respectively generated. Also, 16S rRNA (256-bp) has been used as a polymerase chain reaction control for dove gender identification using the female-specific primer. However, if DNA is degraded or the quality of DNA from samples collected during field research is poor, it may be difficult to amplify a long polymerase chain reaction product that required by the female-specific primer. Therefore, it is possible that some degraded and shorter female DNA samples may not be correctly detected using the female-specific primer. Specifically, if there is only one copy for nucleus genes, the number of mitochondrial may be 1000. Thus, the amount of copies of mitochondrial genes may be about 1000 times that of the nucleus genes. Therefore, as long as one of the 1000 mitochondrials is complete, amplification of the 16S rRNA thereof is possible, i.e., a female may be regarded as a male as their 16S rRNA would be positive and the female-specific polymerase chain reaction would be negative.

Therefore, a high-throughput, and precisely accurate method for Columbidae gender identification is currently needed.

BRIEF SUMMARY OF THE INVENTION

The invention provides a method for Columbidae gender identification comprising: providing a DNA sample of a bird belonging to the Columbidae family; performing a polymerase chain reaction to the DNA sample with a first primer pair of a first primer designed within the region of the SEQ ID. NO.: 9 or a complementary sequence thereof and a P2 primer (SEQ ID. NO: 1) or a complementary sequence thereof, and a second primer pair of a second primer designed within the region of the SEQ ID NO.: 10 or a complementary sequence thereof and a P2 primer (SEQ ID. NO: 1) or a complementary sequence thereof; and determining gender by performing a melting curve analysis to a product from the polymerase chain reaction, wherein the result showing two peaks indicate a female gender and showing one peak indicate a male gender.

The invention provides another method for Columbidae gender identification comprising: providing a DNA sample of a bird belonging to the Columbidae family; performing a polymerase chain reaction to the DNA sample with a first primer pair of a first primer designed within the region of the SEQ ID. NO.: 9 or a complementary sequence thereof and a P2 primer (SEQ ID. NO: 1) or a complementary sequence thereof, and a second primer pair of a second primer designed within the region of the SEQ ID NO.: 10 or a complementary sequence thereof and a P2 primer (SEQ ID. NO: 1) or a complementary sequence thereof; and determining gender by performing an electrophoresis analysis to a product from the polymerase chain reaction, wherein the result showing two bands indicate a female gender and showing one band indicate a male gender.

The invention further provides a nucleotide sequence for Columbidae gender identification, comprising SEQ ID. NO.: 9 or a complementary sequence thereof.

The invention further provides a nucleotide primer pair for Columbidae gender identification, comprising a first primer pair of a first primer designed within the region of the SEQ ID. NO.: 9 or a complementary sequence thereof, and a P2 primer (SEQ ID. NO: 1) or a complementary sequence thereof.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein:

FIGS. 2A-2C show the comparison for CHD-Z and CHD-W gene sequences of *Columba livia, Columba pulchricollis* and *Streptopelia tranquebarica*. The sequences of *C. livia*-Z, *C. pulchricollis*-Z and *S. tranquebarica*-Z are SEQ ID NO: 3, SEQ ID NO: 5 and SEQ ID NO: 7, respectively, while the sequences of *C. livia*-W, *C. pulchricollis*-W and *S. tranquebarica*-W are SEQ ID NO: 4, SEQ ID NO: 6 and SEQ ID NO: 8, respectively. In addition, the sequence of P2 primer is SEQ ID NO: 1 while the sequence of P8 primer [anti-sense] is SEQ ID NO: 13.

DETAILED DESCRIPTION OF THE INVENTION

Figure 1A:
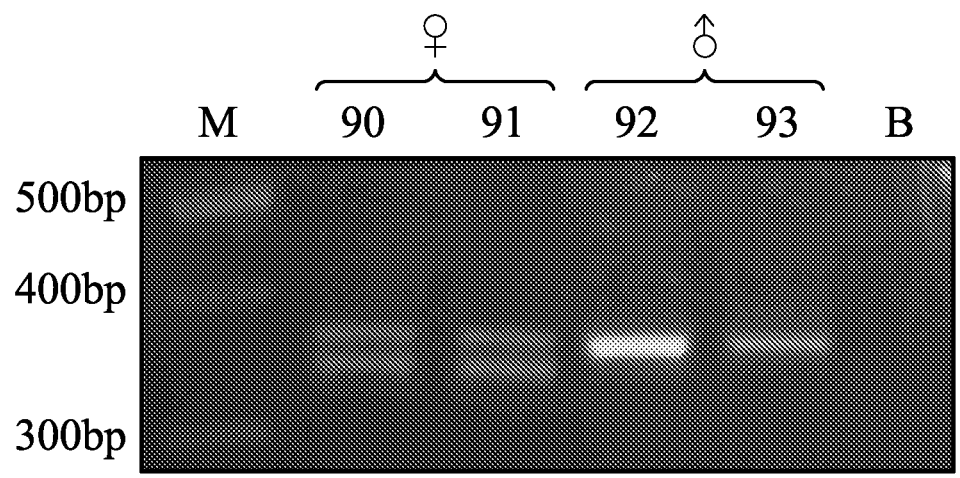
FIGS. 1A-1C show the 3% gel electrophoresis results for products obtained by performing polymerase chain reaction to the DNA samples of *Columba livia, Columba pulchricollis* and *Streptopelia tranquebarica* with P2/P8 primers, respectively.

The following description is of the best-contemplated mode of carrying out the invention. This description is made for the purpose of illustrating the general principles of the invention and should not be taken in a limiting sense. The scope of the invention is best determined by reference to the appended claims.

In the invention, polymerase chain reactions are performed to DNA samples of *Columba livia, Columba pulchricollis* and *Streptopelia tranquebarica* with P2 (5'-TCTG-CATCGCTAAATCCTTT-3') (SEQ ID. NO: 1) (forward)/P8 (5'-CTCCCAAGGATGAGRAAYTG-3') (SEQ ID. NO: 2) (reverse) (Griffiths R, Double M C, Orr K, Dawson R J. (1998) A DNA test to sex most birds. Molecular Ecololgy 7:1071-5), respectively, and products from the polymerase chain reactions are purified by electrophoresis and DNA sequenced.

In the polymerase chain reaction for the DNA samples of *Columba livia*, SEQ ID. NO: 3 with higher molecular weight and SEQ ID. NO: 4 with lower molecular weight are obtained. In the polymerase chain reaction for the DNA samples of *Columba pulchricollis*, SEQ ID. NO: 5 with higher molecular weight and SEQ ID. NO: 6 with lower molecular weight are obtained. In the polymerase chain reaction for the DNA samples of *Streptopelia tranquebarica*, SEQ ID. NO: 7 with higher molecular weight and SEQ ID. NO: 8 with lower molecular weight are obtained. After BLAST analysis, SEQ ID. NOs: 3, 5 and 7 are identified to be very similar to CHD-Z gene of other birds, while SEQ ID. NOs: 4, 6 and 8 are identified to be very similar to the CHD-W gene of other birds, and thus SEQ ID. NOs: 3, 5 and 7 are identified as the CHD-Z gene sequences of *Columba livia, Columba pulchricollis* and *Streptopelia tranquebarica*, respectively, and SEQ ID. NOs: 4, 6 and 8 are identified as the CHD-W gene sequences of *Columba livia, Columba pulchricollis* and *Streptopelia tranquebarica*, respectively.

The conditions for the polymerase chain reaction may be optionally modulated according to different circumstance; however, preferably, the conditions may be: 95° C. (4 min); 95° C. (30 sec, 5 cycles); 47° C. (30 sec); 72° C. (30 sec); 95° C. for (30 sec, 49 cycles); 46° C. (20 sec); 72° C. (20 sec); and 72° C. (5 min).

CHD-Z genes and CHD-W genes of different species of Columbidae are aligned with the aid of a bioinformatics tool, SDSC-Biology Workbench, and then a CHD-ZW common region and a CHD-W specific region are obtained. In one embodiment, the different species of Columbidae may comprise *Columba livia, Columba pulchricollis* and *Streptopelia tranquebarica*. In one embodiment, the CHD-W specific region may be the SEQ ID NO: 9 or a complementary sequence thereof, preferably, and the CHD-ZW common region may be the SEQ ID NO: 10 or a complementary sequence thereof, preferably.

Next, according to the CHD-W specific region, or the CHD-W specific region and CHD-ZW common region, the invention provides a method for Columbidae gender identification.

In one aspect of the invention, Columbidae gender identification is performed by a polymerase chain reaction based melting curve analysis.

In one embodiment, first, a DNA sample of a bird belonging to the Columbidae family may be provided, and a polymerase chain reaction is performed to the DNA sample with a first primer pair of a first primer designed within the region of the SEQ ID. NO.: 9 or a complementary sequence thereof and a P2 primer (SEQ ID. NO: 1) or a complementary sequence thereof. After that, a melting curve analysis is performed to a product from the polymerase chain reaction, wherein the result shows one peak indicating a female gender and no peak indicating a male gender or that the DNA quality is poor and undeterminable. At this time, in order to confirm that the gender of the Columbidae is male, another embodiment in the following may be adopted.

In another embodiment, first, a DNA sample of a bird belonging to the Columbidae family may be provided, and a polymerase chain reaction is performed to the DNA sample with a first primer pair of a first primer designed within the region of the SEQ ID. NO.: 9 or a complementary sequence thereof and a P2 primer (SEQ ID. NO: 1) or a complementary sequence thereof, and a second primer pair of a second primer designed within the region of the SEQ ID NO.: 10 or a complementary sequence thereof and a P2 primer (SEQ ID. NO: 1) or a complementary sequence thereof. After that, a melting curve analysis is performed to a product from the polymerase chain reaction, wherein the result shows the two peaks indicating a female gender and the one peak indicating a male gender.

Examples of the first primer pair may comprise the complementary sequence of the SEQ ID. NO.: 9 (reverse) and the P2 primer (SEQ ID. NO: 1) (forward), or SEQ ID. NO.: 9 (forward) and the complementary sequence of the P2 primer (SEQ ID. NO: 1) (reverse). Moreover, examples of the first primer pair may also comprise a complementary sequence of the SEQ ID. NO.: 11 (reverse) and the P2 primer (SEQ ID. NO: 1) (forward), or SEQ ID. NO.: 11 (forward) and the complementary sequence of the P2 primer (SEQ ID. NO: 1) (reverse). In addition, examples of the second primer pair may comprise the complementary sequence of the SEQ ID. NO.: 10 (reverse) and the P2 primer (SEQ ID. NO: 1) (forward), or SEQ ID. NO.: 10 (forward) and the complementary sequence of the P2 primer (SEQ ID. NO: 1) (reverse). Moreover, examples of the second primer pair may also comprise a complementary sequence of the SEQ ID. NO.: 12 (reverse) and the P2 primer (SEQ ID. NO: 1) (forward), or SEQ ID. NO.: 12 (forward) and the complementary sequence of the P2 primer (SEQ ID. NO: 1) (reverse).

Because the female gender of a bird belonging to the Columbidae family has both the CHD-Z gene and CHD-W gene, when the sample is of a female gender and the first primer pair of the first primer (within the CHD-W specific region)/P2 primer or the complementary sequence thereof is used to perform the polymerase chain reaction, the female DNA sample will generate one polymerase chain reaction product segment, which is a polymerase chain reaction product generated from the first primer pair of the first primer (within the CHD-W specific region)/P2 primer or the complementary sequence thereof. Therefore, when a melting curve analysis is performed to the polymerase chain reaction product, a melting curve will be generated with one peak. Furthermore, when the sample is obtained from a female gender and the first primer pair of the first primer (within the CHD-W specific region)/P2 primer or the complementary sequence thereof and the second primer pair of the second primer (within the CHD-ZW common region)/P2 primer or the complementary sequence thereof are used simultaneously to perform the polymerase chain reaction, the female DNA sample will generate two polymerase chain reaction product segments, which is a polymerase chain reaction product generated from the first primer pair of the first primer (within the CHD-W specific region)/P2 primer or the complementary sequence thereof and the second primer pair of the second primer (within the CHD-ZW common region)/P2 primer or the complementary sequence thereof, respectively. Therefore, when a melting curve analysis is performed to the polymerase chain reaction product, the two polymerase chain reaction product segments will generate two melting curves (each polymerase chain reaction product segment has one melting curve) and have two peaks (each melting curve has one peak). In one embodiment, the product generated from the first primer pair of the first primer (the complementary sequence of the SEQ ID. NO: 11, within the CHD-W specific region) (reverse)/P2 primer (forward) is about 252-b.p. and the product generated from the second primer pair of the second primer (the complementary sequence of the SEQ ID. NO: 12, within the CHD-ZW common region) (reverse)/P2 primer (forward) is about 104-b.p.

The male gender of a bird belonging to the Columbidae family only has a CHD-Z gene, and thus when the first primer pair of the first primer (within the CHD-W specific region)/P2 primer or the complementary sequence thereof is used to perform the polymerase chain reaction, the male DNA sample is not able to generate a polymerase chain reaction product. Therefore, when a melting curve analysis is performed, no melting curve will be generated with no peaks. Furthermore, when the sample is of a male and the first primer pair of the first primer (within the CHD-W specific region)/P2 primer or the complementary sequence thereof and the second primer pair of the second primer (within the CHD-ZW common region)/P2 primer or the complementary sequence thereof are used simultaneously to perform the polymerase chain reaction, the male DNA sample will only generate one polymerase chain reaction product segment, which is a polymerase chain reaction product generated from the second primer pair of the second primer (within the CHD-ZW common region)/P2 primer or the complementary sequence thereof. Therefore, when a melting curve analysis is performed to the polymerase chain reaction product, only one melting curve will be generated with only one peak. In one embodiment, the product generated from the second primer pair of the second primer (the complementary sequence of the SEQ ID. NO: 12, within the CHD-ZW common region) (reverse)/P2 primer (forward) is about 104-b.p.

Since DNA of a female or a male may be used to perform a polymerase chain reaction with the second primer pair of the second primer (within the CHD-ZW common region)/P2 primer or the complementary sequence thereof to generate a product, the polymerase chain reaction performed with the second primer pair of the second primer (within the CHD-ZW common region)/P2 primer or the complementary sequence thereof may be used as a positive control.

According to the differences of the primer used and diversity of the Columbidae to be identified, the differences in length between products from the first primer/P2 primer or the complementary sequence thereof and the second primer/P2 primer or the complementary sequence thereof is at least greater than abut 100-b.p. Therefore, when the two primer pairs are used to perform a polymerase chain reaction simultaneously and then melting curve analysis is performed, the two peaks are able to be clearly separated. In one embodiment, the differences in length between the product from the first primer/P2 primer or the complementary sequence thereof (252-b.p.) and product from the second primer/P2 primer or the complementary sequence thereof (104-b.p.) is abut 148-b.p. Moreover, in one embodiment, the melting temperature (peak) of the product from the first primer /P2 primer or the complementary sequence thereof is about 78.5-

79.5° C., and the melting temperature (peak) of the product from the second primer /P2 primer or the complementary sequence thereof is about 77-78° C. The melting temperature difference of the two peaks may be about 0.5-2.5° C., and in one embodiment is about 1.5° C.

All birds belonging to the Columbidae family may be used by the method to identify gender thereamong. In one embodiment, a bird belonging to the Columbidae family may comprise *Columba livia, Columba pulchricollis* or *Streptopelia tranquebarica*.

The polymerase chain reaction may be modulated according to the circumstances and have no particular limitations. Furthermore, the polymerase chain reaction mentioned above may be a typical polymerase chain reaction or a real-time polymerase chain reaction. If a typical polymerase chain reaction is preformed, the step needed for performing the melting curve analysis may be performed after the polymerase chain reaction is completed. If a real-time polymerase chain reaction is preformed, a melting curve analysis may be performed immediately in the same machine that the polymerase chain reaction has been preformed after the polymerase chain reaction is completed. Compared with the typical polymerase chain reaction method, a polymerase chain reaction based melting curve analysis, only an additional fluorescent reagent is needed to be added therein, such as am SYBR green I.

The method using the melting curve analysis of the invention does not require electrophoresis analysis and has advantages of high-throughput (96-or 384 well polymerase chain reaction may be selected) and time savings.

In another aspect of the invention, Columbidae gender identification is performed by a polymerase chain reaction based electrophoresis analysis.

In one embodiment, first, a DNA sample of a bird belonging to the Columbidae family may be provided, and a polymerase chain reaction is performed to the DNA sample with a first primer pair of a first primer designed within the region of the SEQ ID. NO.: 9 or a complementary sequence thereof and a P2 primer (SEQ ID. NO: 1) or a complementary sequence thereof. After that, an electrophoresis analysis is performed to a product from the polymerase chain reaction, wherein the result shows the one band indicating a female gender and no band indicating a male gender or that the DNA quality is poor and undeterminable. At this time, in order to confirm that the gender of the Columbidae is male, another embodiment in the following may be adopted.

In another embodiment, first, a DNA sample of a bird belonging to the Columbidae family may be provided, and a polymerase chain reaction is performed to the DNA sample with a first primer pair of a first primer designed within the region of the SEQ ID. NO.: 9 or a complementary sequence thereof and a P2 primer (SEQ ID. NO: 1) or a complementary sequence thereof, and a second primer pair of a second primer designed within the region of the SEQ ID NO.: 10 or a complementary sequence thereof and a P2 primer (SEQ ID. NO: 1) or a complementary sequence thereof. After that, an electrophoresis analysis is performed to a product from the polymerase chain reaction, wherein the result shows the two bands indicating a female gender and the one band indicating a male gender.

Examples of the first primer pair may comprise the complementary sequence of the SEQ ID. NO.: 9 (reverse) and the P2 primer (SEQ ID. NO: 1) (forward), or SEQ ID. NO.: 9 (forward) and the complementary sequence of the P2 primer (SEQ ID. NO: 1) (reverse). Moreover, examples of the first primer pair may also comprise a complementary sequence of the SEQ ID. NO.: 11 (reverse) and the P2 primer (SEQ ID. NO: 1) (forward), or SEQ ID. NO.: 11 (forward) and the complementary sequence of the P2 primer (SEQ ID. NO: 1) (reverse). In addition, examples of the second primer pair may comprise the complementary sequence of the SEQ ID. NO.: 10 (reverse) and the P2 primer (SEQ ID. NO: 1) (forward), or SEQ ID. NO.: 10 (forward) and the complementary sequence of the P2 primer (SEQ ID. NO: 1) (reverse). Moreover, examples of the second primer pair may also comprise a complementary sequence of the SEQ ID. NO.: 12 (reverse) and the P2 primer (SEQ ID. NO: 1) (forward), or SEQ ID. NO.: 12 (forward) and the complementary sequence of the P2 primer (SEQ ID. NO: 1) (reverse).

Because the female gender of a bird belonging to the Columbidae family has both the CHD-Z gene and CHD-W gene, when the sample is of a female gender and the first primer pair of the first primer (within the CHD-W specific region)/P2 primer or the complementary sequence thereof is used to perform the polymerase chain reaction, the female DNA sample will generate one polymerase chain reaction product segment, which is a polymerase chain reaction product generated from the first primer pair of the first primer (within the CHD-W specific region)/P2 primer or the complementary sequence thereof. Therefore, when an electrophoresis analysis is performed to the polymerase chain reaction product, one product will be generated and have one band. Furthermore, when the sample is obtained from a female gender and the first primer pair of the first primer (within the CHD-W specific region)/P2 primer or the complementary sequence thereof and the second primer pair of the second primer (within the CHD-ZW common region)/P2 primer or the complementary sequence thereof are used simultaneously to perform the polymerase chain reaction, the female DNA sample will generate two polymerase chain reaction product segments, which is a polymerase chain reaction products generated from the first primer pair of the first primer (within the CHD-W specific region)/P2 primer or the complementary sequence thereof and the second primer pair of the second primer (within the CHD-ZW common region)/P2 primer or the complementary sequence thereof, respectively. Therefore, when an electrophoresis analysis is performed to the polymerase chain reaction product, two bands will be generated. In one embodiment, the product generated from the first primer pair of the first primer (the complementary sequence of the SEQ ID. NO: 11, within the CHD-W specific region) (reverse)/P2 primer (forward) is about 252-b.p. and the product generated from the second primer pair of the second primer (the complementary sequence of the SEQ ID. NO: 12, within the CHD-ZW common region) (reverse)/P2 primer (forward) bout 104-b.p.

The male gender of a bird belonging to the Columbidae family only has a CHD-Z gene, and thus when the first primer pair of the first primer (within the CHD-W specific region)/P2 primer or the complementary sequence thereof is used to perform the polymerase chain reaction, the male DNA sample is not able to generate a polymerase chain reaction product. Therefore, when an electrophoresis analysis is performed, no band will appear. Furthermore, when the sample is of a male gender and the first primer pair of the first primer (within the CHD-W specific region)/P2 primer or the complementary sequence thereof and the second primer pair of the second primer (within the CHD-ZW common region)/P2 primer or the complementary sequence thereof are used simultaneously to perform the polymerase chain reaction, the male DNA sample will only generate one polymerase chain reaction product segment, which is a polymerase chain reaction products generated from the second primer pair of the second primer (within the CHD-ZW common region)/P2 primer or the complementary sequence thereof. Therefore, when an electrophoresis analysis is performed to the polymerase chain reaction product, only one band will appear. In one embodiment, the product generated from the second primer pair of the second primer (the complementary sequence of the SEQ ID. NO: 12, within the CHD-ZW common region) (reverse)/P2 primer (forward) is about 104-b.p.

On the other hand, since the DNA of a female or male gender both, are able to be used to perform a polymerase chain reaction with the second primer pair of the second primer (within the CHD-ZW common region)/P2 primer or the complementary sequence thereof to generate a product, the polymerase chain reaction performed with the second primer pair of the second primer (within the CHD-ZW common region)/P2 primer or the complementary sequence thereof may be used as a positive control.

According to the differences of the primer used and diversity of the Columbidae to be identified, the differences in length between products from the first primer/P2 primer or the complementary sequence thereof and the second primer/P2 primer or the complementary sequence thereof is at least greater than abut 100-b.p. Therefore, when the two primer pairs are used to perform a polymerase chain reaction simultaneously and then electrophoresis analysis is performed, the two bands are able to be clearly separated. In one embodiment, the differences in length between the product from the first primer/P2 primer or the complementary sequence thereof (252-b.p.) and product from the second primer/P2 primer or the complementary sequence thereof (104-b.p.) is abut 148-b.p.

All birds belonging to the Columbidae family may be used by the method to identify gender thereamong. In one embodiment, a bird belonging to the Columbidae family may comprise *Columba livia, Columba pulchricollis* or *Streptopelia tranquebarica*.

The polymerase chain reaction may be modulated according to the circumstances and have no particular limitations.

According to the foregoing, it is known that the gender of a bird belonging to the Columbidae family may be identified by using the CHD-W specific region, or CHD-W specific region and CHD-ZW common region. Accordingly, the invention may further provide a nucleotide sequence for Columbidae gender identification which may comprise a CHD-W specific region and CHD-ZW common region CHD-W specific region, or CHD-W specific region and CHD-ZW common region. In one embodiment, a nucleotide sequence for Columbidae gender identification provided by the invention may comprise SEQ ID. NO.: 9 or a complementary sequence thereof, or may further comprise SEQ ID. NO.: 10 or a complementary sequence thereof.

According to the foregoing, the invention may further provide a nucleotide primer pair for Columbidae gender identification, which may comprise a first primer pair of a first primer designed within the region of the SEQ ID. NO.: 9 or a complementary sequence thereof, and a P2 primer (SEQ ID. NO: 1) or a complementary sequence thereof, or may further comprise a second primer designed within the region of the SEQ ID. NO.: 10 or a complementary sequence thereof, and a P2 primer (SEQ ID. NO: 1) or a complementary sequence thereof.

Examples of the first primer pair may comprise the complementary sequence of the SEQ ID. NO.: 9 (reverse) and the P2 primer (SEQ ID. NO: 1) (forward), or SEQ ID. NO.: 9 (forward) and the complementary sequence of the P2 primer (SEQ ID. NO: 1) (reverse). Moreover, examples of the first primer pair may also comprise a complementary sequence of the SEQ ID. NO.: 11 (reverse) and the P2 primer (SEQ ID. NO: 1) (forward), or SEQ ID. NO.: 11 (forward) and the complementary sequence of the P2 primer (SEQ ID. NO: 1) (reverse). In addition, examples of the second primer pair may comprise the complementary sequence of the SEQ ID. NO.: 10 (reverse) and the P2 primer (SEQ ID. NO: 1) (forward), or SEQ ID. NO.: 10 (forward) and the complementary sequence of the P2 primer (SEQ ID. NO: 1) (reverse). Moreover, examples of the second primer pair may also comprise a complementary sequence of the SEQ ID. NO.: 12 (reverse) and the P2 primer (SEQ ID. NO: 1) (forward), or SEQ ID. NO.: 12 (forward) and the complementary sequence of the P2 primer (SEQ ID. NO: 1) (reverse).

EXAMPLE

1. Sample Source and DNA Extraction

Muscle tissue samples for male-female paired *Columba livia* (females (Bd90 and Bd91) and males (Bd92 and Bd93)), *Columba pulchricollis* (female (Bd5137) and males (Bd3314, Bd4970, and Bd5417)), and *Streptopelia tranquebarica* (female (Bd101) and male (Bd102)), which died due to collision, were collected from the Taiwan Endemic Species Research Institute. Following, the genders of the samples were determined by anatomical inspection. Next, tissue DNAs were extracted by a DNeasy tissue kit (Qiagen, Valencia, Calif., USA) according to instructions.

2. Primary Molecular Gender Identification by Griffiths P2/P8 Primer Set

Polymerase Chain Reaction

The P2 (SEQ ID. NO: 1) (forward)/P8 (SEQ ID. NO: 2) (reverse) primers (Griffiths) for molecular gender identification of birds were used for the three species belonging to the Columbidae family. A polymerase chain reaction cocktail contained a 1× polymerase chain reaction buffer, 0.16 μM primers, 0.2 mM dNTPs, 0.7U Platinum-Taq enzyme (Invitrogen), 1.5 mM $MgCl_2$, SYBGreen I (1:2000; Invitrogen), and 10-20 ng DNA in a total volume of 10 μl. The polymerase chain reaction program was as described: 95° C. (4 min); 95° C. (30 sec, 5 cycles); 47° C. (30 sec); 72° C. (30 sec); 95° C. for (30 sec, 49 cycles); 46° C. (20 sec); 72° C. (20 sec); and 72° C. (5 min).

(1) Electrophoresis Analysis

Figure 1B:
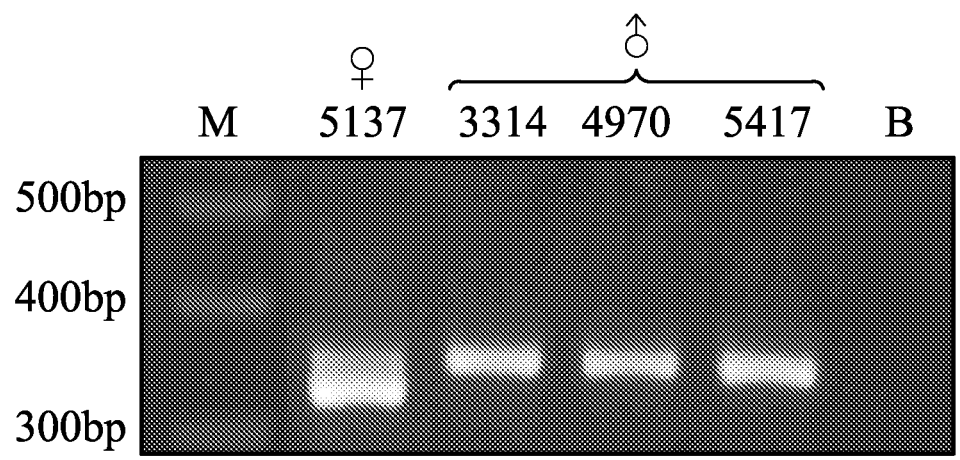
Figure 1C:
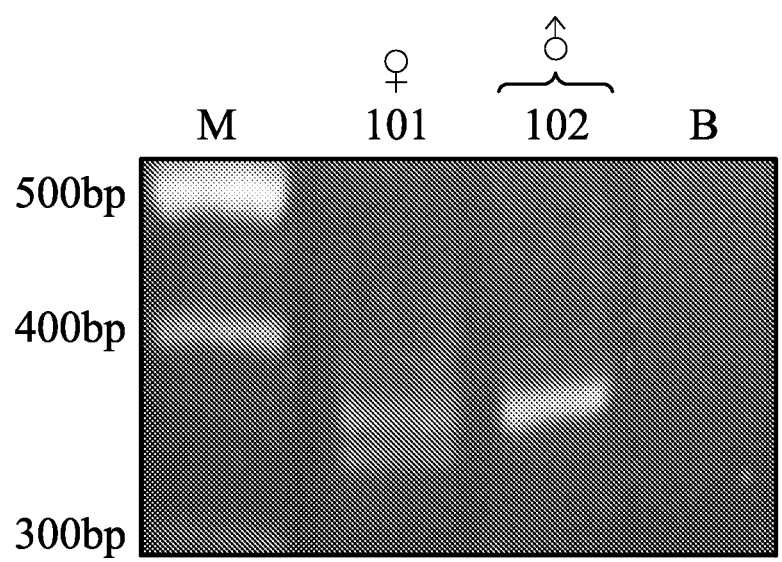

The polymerase chain reaction products (CHD-Z and CHW amplicons) were used to perform an electrophoresis analysis, and the results are shown as FIGS. 1A-1C. In FIGS. 1A to 1C, the three species belonging to the Columbidae family (*Columba livia, Columba pulchricollis* and *Streptopelia tranquebarica. C. livia*) in 3% gel electrophoresis, display that those of a female gender had two specific bands representing the CHD-Z (top) and CHD-W (bottom) and those of a male gender only had one specific band representing the CHD-Z.

(2) Melting Curve Analysis

Following completion of the polymerase chain reaction, a melting curve was analyzed with a default program of the iQ™5 real-time polymerase chain reaction machine (Bio-Rad Laboratories, Hercules, Calif.), i.e., 55° C. to 95° C. with a heating rate of 0.5° C./s for 80 repeated counts. Melting curve data were represented as −dF/dT vs. T (F and T are regarded as the fluorescence and temperature). The melting temperature (Tm; the temperature corresponding to the peak for −dF/dT) for each polymerase chain reaction product was determined by a Bio-Rad iQ5 default software. RFU represents relative fluorescence unit.

Figure 1D:
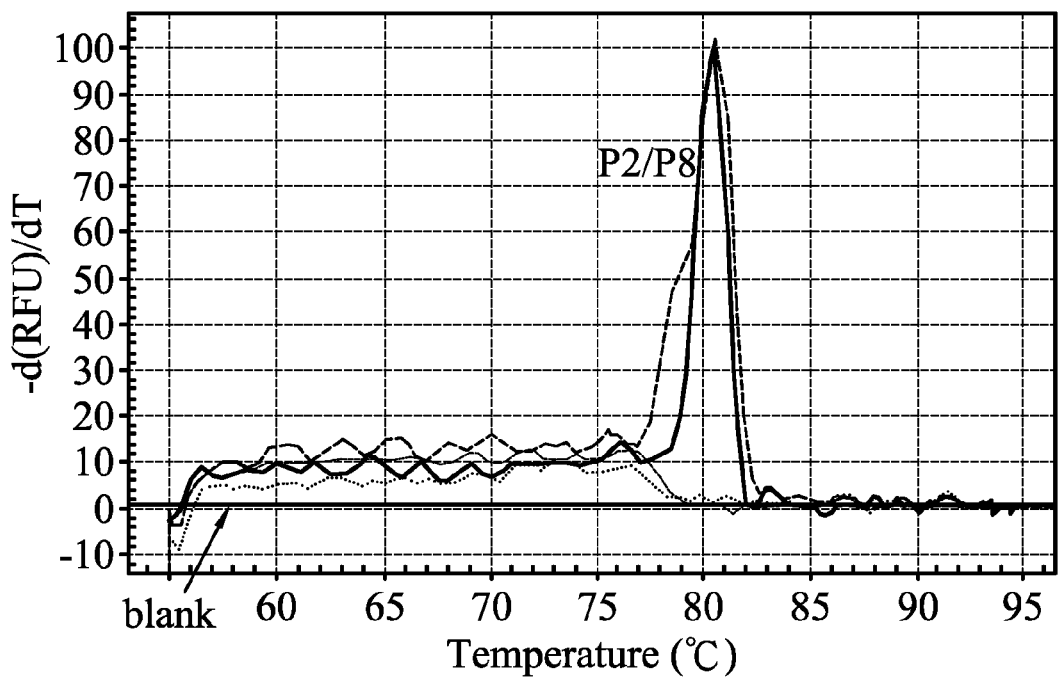
FIGS. 1D-1F show the melting curve analysis results for products obtained by performing polymerase chain reaction to the DNA samples of *Columba livia, Columba pulchricollis* and *Streptopelia tranquebarica* with P2/P8 primers, respectively.
Figure 1E:
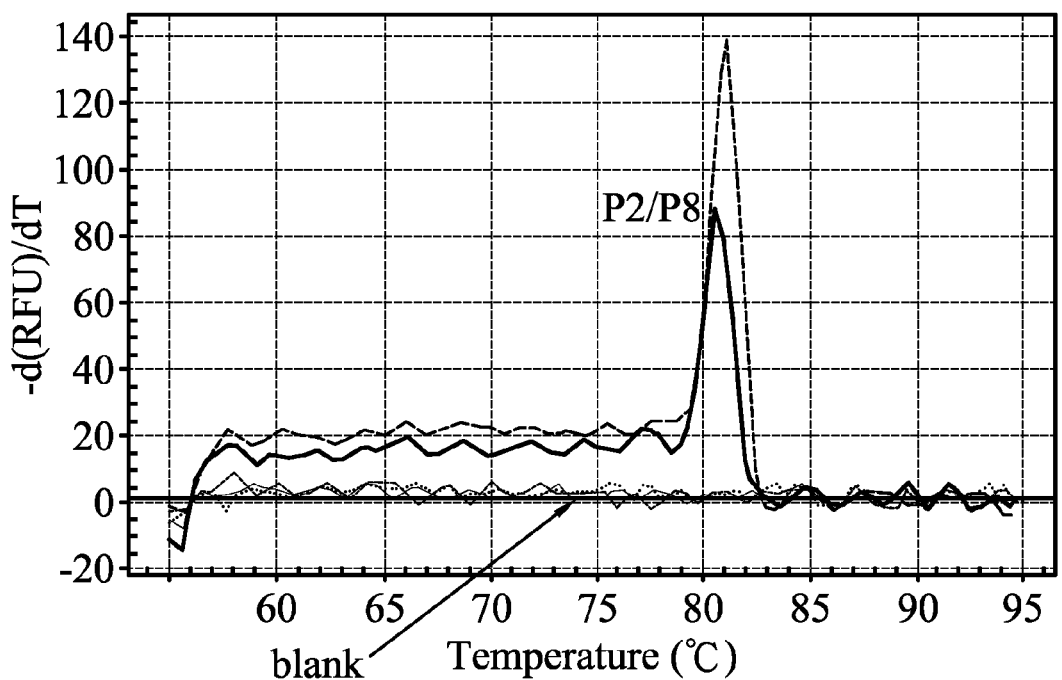
Figure 1F:
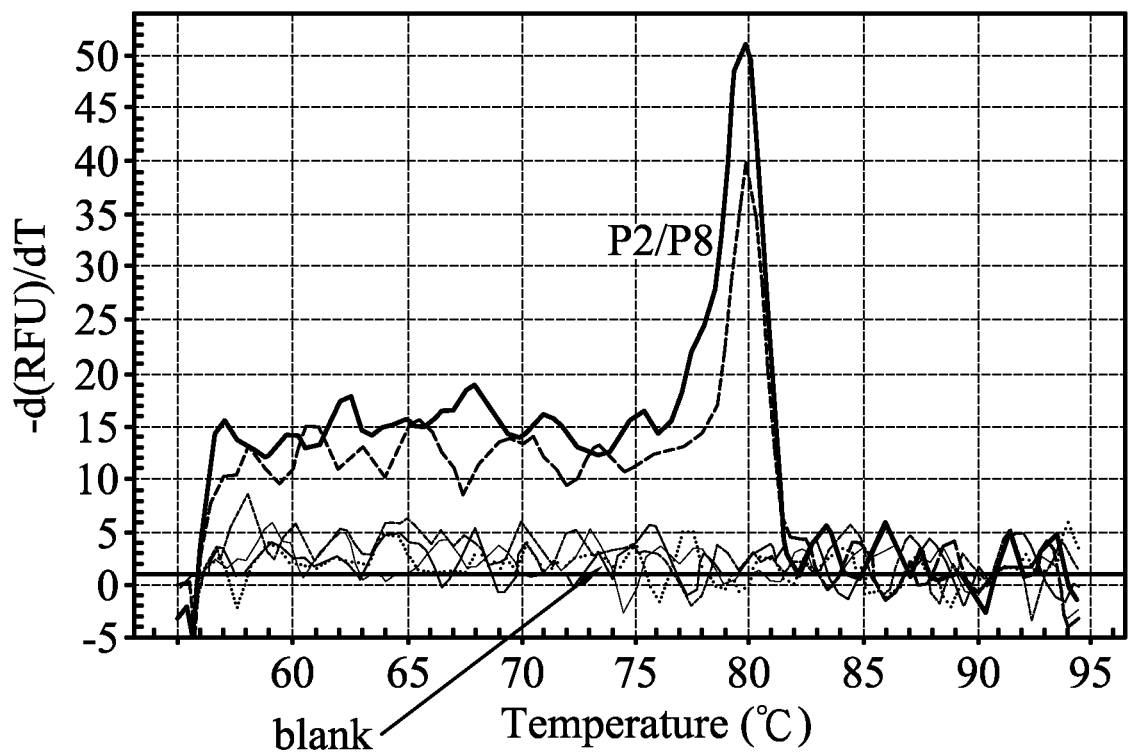

For the melting curve analysis of the P2/P8 polymerase chain reaction amplicons (CHD-Z and/or CHD-W genes) of the species of the Columbidae, there was only one Tm peak at about 80° C., which was undistinguishable for both the female and male gender of the birds belonging to the Columbidae. The results are shown as FIGS. 1D to 1F. FIGS. 1D to 1F are the results for *Columba livia, Columba pulchricollis* and *Streptopelia tranquebarica*, respectively and show Tm values of P2/P8 amplicons of both the female gender (Bds 91, 5137 and 101) and male gender (Bds 93 and 5417) for *C. livia, C. pulchricollis*, and *S. tranquebarica* were similar (80.0 to 80.5° C.). Therefore, melting curve analysis could not be performed when using the P2/P8 primer set when the gender of the *Columba livia, Columba pulchricollis* and *Streptopelia tranquebarica* were tested.

3. Sequencing of the CHD-Z and CHD-W Amplicons

For sequencing, DNA in the gel mentioned above was extracted by a gel extraction kit (Qiagen). Then the sequencing was performed. The results for the sequencing are shown in FIGS. 2A-2C. Referring to FIGS. 2A-2C, SEQ ID NO: 3 (*C. livia*-Z) with higher molecular weight and SEQ ID NO: 4 (*C. livia*-W) with lower molecular weight for *Columba livia* were obtained, SEQ ID NO: 5 (*C. pulchricollis*-Z) with higher molecular weight and SEQ ID NO: 6 (*C. pulchricollis*-W) with lower molecular weight for *Columba pulchricollis* were obtained, SEQ ID NO: 7 (*S. tranquebarica*-Z) with higher molecular weight and SEQ ID NO: 8 (*S. Tranquebarica*-W) with lower molecular weight for *Streptopelia tranquebarica* were obtained. Moreover, the sequence of P2 primer in FIGS. 2A is SEQ ID NO: 1, the sequence of P8 primer [anti-sense] in FIGS. 2C is SEQ ID NO: 13.

4. Calculation of the Differences in Length of Intron Between CHD-Z and CHD-W Amplicons Sequences were aligned with the aid of a bioinformatics tool, SDSC-Biology Workbench. The results are shown in FIGS. 2A-2C. The differences in length of intron between the CHD-Z and CHD-W amplicons using a Griffiths P2/P8 primer set for each species was calculated as described in Chang, H. W., Gu, D. L., Su, S. H., Chang, C. C., Cheng, C. A., Huang, H. W., Yao, C. T., Chou, T. C., Chuang, L. Y. and Cheng, C. C. (2008) High-throughput gender identification of Accipitridae eagles with real-time polymerase chain reaction using TaqMan probes. Theriogenology, 70, 83-90. In brief, the deleted regions (indicated by dash lines in FIGS. 2A-2C) within the sequences for the CHD-Z and CHD-W amplicons were calculated from the pre-aligned sequences of the same species.

CHD-Z and CHD-W genes of *Columba livia, Columba pulchricollis* and *Streptopelia tranquebarica* are represented as CHD-Z/CHD-W (the differences in length between the two genes). *Columba livia*: SEQ ID. NO.: 3/SEQ ID. NO.: 4 (20-bp), *Columba pulchricollis*: SEQ ID. NO.: 5/SEQ ID. NO.: 6 (21-bp), and *Streptopelia tranquebarica*: SEQ ID. NO.: 7/SEQ ID. NO.: 8 (18-bp).

After comparing every gene sequences, differences in length of polymerase chain reaction products for CHD-Z and CHD-W gene obtained by using the P2/P8 primers was only about 18-21 b.p., which indicated that the P2/P8 primers were not suitable for Columbidae gender identification.

In addition, according to the sequence alignment mentioned above, a CHD-W specific sequence was obtained and named as a CHD-W specific region which is SEQ ID. NO.: 9 as shown as a black box region 1 of FIG. 2B, a CHD-ZW common sequence was obtained and named as a CHD-ZW common region which is SEQ ID. NO.: 10 as shown as a black box region 2 of FIG. 2A.

5. Secondary Molecular Gender Identification Using Re-Designed Primers

To solve the intrinsic problems of performing melting curve analysis (FIG. 1) in gender identification using a P2/P8 primer set, a polymerase chain reaction reverse primer for the CHD-W specific region and the CHD-ZW common region for the three species belonging to the Columbidae family were re-designed within the CHD-W specific region (SEQ ID. NO.: 9) and CHD-ZW common region (SEQ ID. NO.: 10), respectively to increase differences in length between the polymerase chain reaction products. The reverse primer for the CHD-W specific region was SEQ ID. NO.: 11, and the reverse primer for the CHD-ZW common region was SEQ ID. NO.: 12. The primer designed within the CHD-W specific region/P2 primer were designed to be female-specific and the primer designed within the CHD-ZW common region /P2 primer were regarded as the positive polymerase chain reaction control for both female and male gender identification. The polymerase chain reaction products amplified by SEQ ID. NO.: 11 (within the CHD-W specific region) primer (reverse)/P2 (forward) were 252-bp, and SEQ ID. NO.: 12 (within the CHD-ZW common region) primer (reverse)/P2 (forward) were 104-bp.

Polymerase Chain Reaction

The polymerase chain reaction program was slightly modified in comparison to the primary molecular gender identification (mentioned above) as follows: denaturation (95° C., 3 min), denaturation (95° C., 30 sec, 50 cycles), annealing (58° C., 30 sec), and extension (72° C., 15 sec).

(1) Electrophoresis Analysis

Figure 3A:
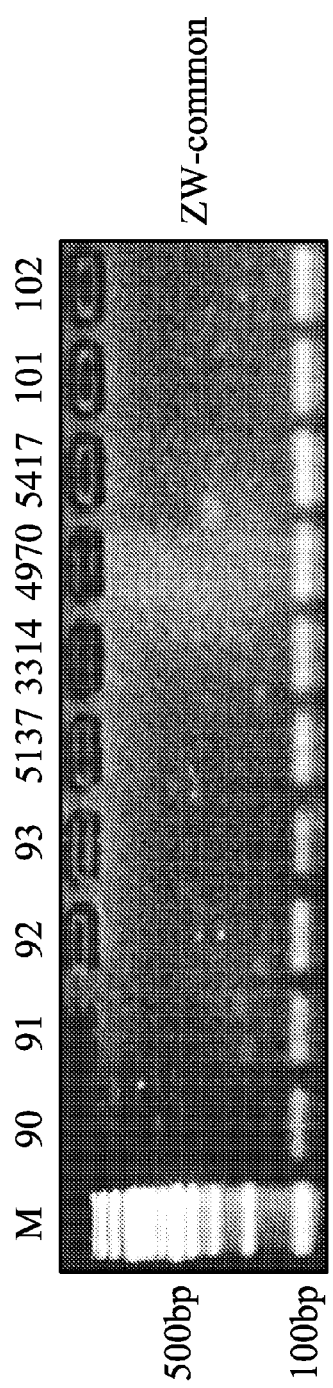
FIGS. 3A-3B show the 1.5% gel electrophoresis results for products obtained by performing polymerase chain reaction to the DNA samples of *Columba livia, Columba pulchricollis* and *Streptopelia tranquebarica* with the re-designed primers of the invention, respectively.
Figure 3B:
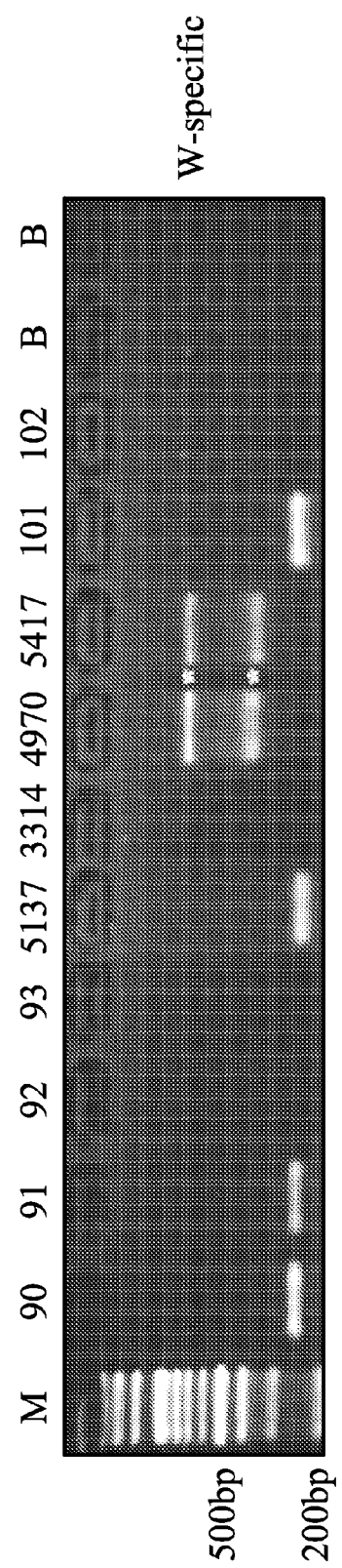

To test the performance of re-designed sex-specific primers, a polymerase chain reaction was amplified by the primer designed within the CHD-W specific region/P2 primer and the primer designed within the CHD-ZW common region /P2 primer in different polymerase chain reaction-wells and the polymerase chain reaction amplicons were examined in 1.5% agarose gel. The results are shown as FIGS. 3A and 3B, respectively. The female birds (CHD-Z/CHD-W type), such as Bds 90, 91, 5137, and 101, were correctly amplified for both polymerase chain reaction reactions using the primer designed within the CHD-W specific region/P2 primer and the primer designed within the CHD-ZW common region /P2 primer. However, the male birds (CHD-Z/CHD-Z type) were only correctly amplified for the primer designed within the CHD-ZW common region /P2 primer but not for polymerase chain reaction using the primer designed within the CHD-W specific region/P2 primer. Although some of the male genders (Bds 4970 and 5417) showed some non-specific bands with incorrect sizes using the primer designed within the CHD-W specific region/P2 primer (indicated by star in FIG. 3B), the non-specific polymerase chain reaction products were sequenced and performed BLAST for identification that they were not homologous to CHD genes (data not shown).

(2) High-Throughput Molecular Gender Identification of the Three Species Belonging to the Columbidae Family—Melting Curve Analysis Following completion of the polymerase chain reaction, a melting curve was analyzed with the default program of the iQ™5 real-time polymerase chain reaction machine (Bio-Rad Laboratories, Hercules, Calif.), i.e., 55° C. to 95° C. with a heating rate at 0.5° C./s for 80 repeated counts. Melting curve data were represented as $-dF/dT$ vs. T (F and T are regarded as the fluorescence and temperature). The melting temperature (Tm; the temperature corresponding to the peak for $-dF/dT$) for each polymerase chain reaction product was determined by a Bio-Rad iQ5 default software. RFU represents relative fluorescence unit. Melting curve analysis data were duplicately experimented. The results are shown in FIGS. 3C and 3D.

Figure 3C:
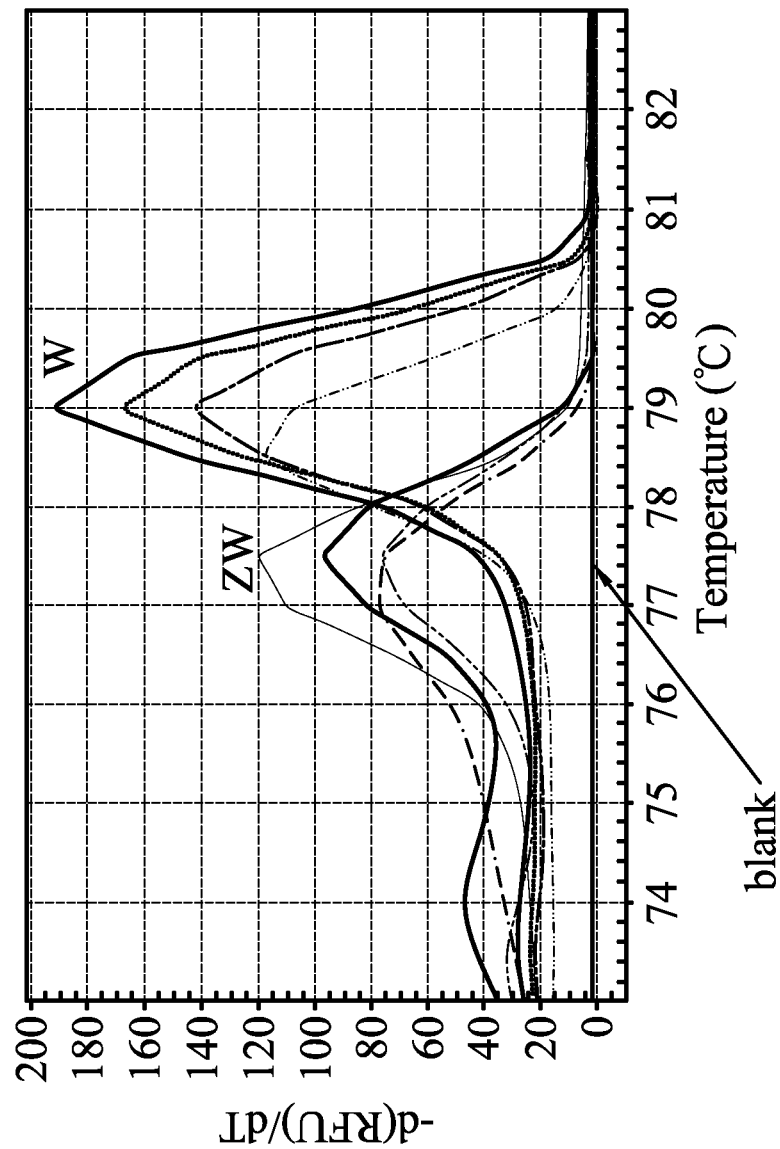
FIGS. 3C-3D show the melting curve analysis results for products obtained by performing polymerase chain reaction to the DNA samples of *Columba livia, Columba pulchricollis* and *Streptopelia tranquebarica* with the re-designed primers of the invention, respectively
Figure 3D:
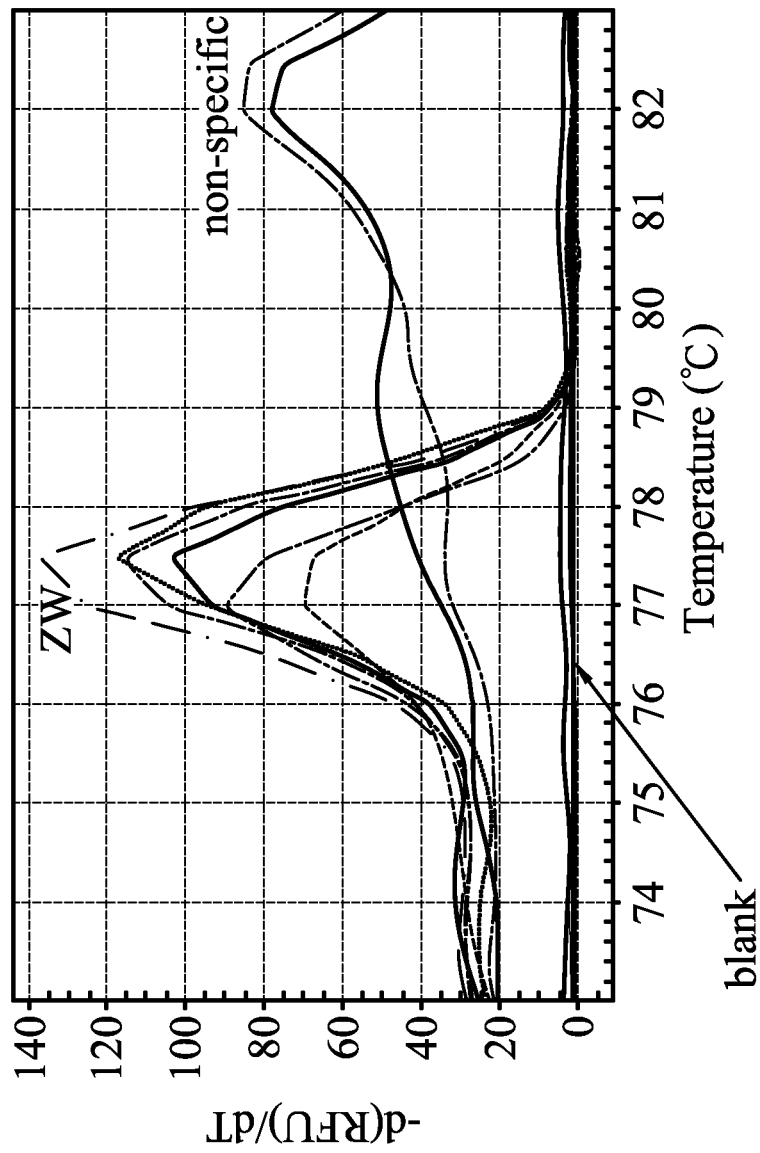

In FIGS. 3C and 3D, the melting curve analysis for the same polymerase chain reaction (FIGS. 3A and 3B) was performed. In FIG. 3C, four females (Bds 90, 91, 5137 and 101) were used to perform a melting curve analysis and the result showed that the four individual females of the three species belonging to the Columbidae family were all determined to be of a female gender because they displayed both peaks for the primer designed within CHD-W specific region/ P2 primer and the primer designed within the CHD-ZW common region /P2 primer (W:79.0-79.5° C.; ZW: 77.5° C.). In contrast, six males (Bds 92, 93, 3314, 4970, 5417 and 102)) were used to perform a melting curve analysis and the result showed that the six individual females of the three species belonging to the Columbidae family were all determined to be of a male gender because they displayed a single peak for the primer designed within the CHD-ZW common region /P2 primer (ZW: 77.5° C.).

For certain males (Bds 4970 and 5417), non-specific polymerase chain reaction amplification using the primer designed within CHD-W specific region/P2 primer were found but were discriminated to the primer designed within CHD-W specific region/P2 primer and the primer designed within the CHD-ZW common region /P2 primer products by their different Tm values (77.5 and 79.0-79.5 vs. 82.0° C. (FIG. 3D).

Using the re-designed sex-specific primers, the primer designed within CHD-W specific region/P2 primer and primer designed within the CHD-ZW common region /P2 primer, the differences in length between two polymerase chain reaction amplicons for the species belonging to the Columbidae family were extended to 148-b.p. (FIGS. 2A-2C) to resolve the different curves resulted from the melting curve analysis (FIG. 3).

Although nonspecific amplification was observed in the primer designed within the CHD-W specific region/P2 primer for some male samples (FIG. 3), it was still easy to distinguish the nonspecific amplicon with the target polymerase chain reaction amplicons based on the Tm values.

Accordingly, the re-designed sex-specific primers of the invention may be used to perform a method for Columbidae gender high-throughput identification using melting curve analysis.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method for Columbidae gender identification comprising:
 providing a DNA sample of a bird belonging to the Columbidae family;
 performing a polymerase chain reaction to the DNA sample with a first primer pair of a first primer designed within the region of the SEQ ID NO: 9 or the complementary sequence thereof and a P2 primer (SEQ ID NO: 1) or the complementary sequence thereof, and a second primer pair of a second primer designed within the region of the SEQ ID NO: 10 or the complementary sequence thereof and a P2 primer (SEQ ID NO: 1) or the complementary sequence thereof; and
 determining gender by performing a melting curve analysis to a product from the polymerase chain reaction, wherein the result showing two peaks indicates a female gender and the result showing one peak indicates a male gender.

2. The method for Columbidae gender identification as claimed in claim 1, wherein the Columbidae comprises *Columba livia, Columba pulchricollis* or *Streptopelia tranquebarica*.

3. The method for Columbidae gender identification as claimed in claim 1, wherein the first primer pair comprises the complementary sequence of the SEQ ID NO: 9 and the P2 primer (SEQ ID NO: 1), or SEQ ID NO: 9 and the complementary sequence of the P2 primer (SEQ ID NO: 1).

4. The method for Columbidae gender identification as claimed in claim 1, wherein the second primer pair comprises the complementary sequence of the SEQ ID NO: 10 and the P2 primer (SEQ ID NO: 1), or SEQ ID NO: 10 and the complementary sequence of the P2 primer (SEQ ID NO: 1).

5. The method for Columbidae gender identification as claimed in claim 1, wherein the first primer pair comprises the complementary sequence of the SEQ ID NO: 11 and the P2 primer (SEQ ID NO: 1), or SEQ ID NO: 11 and the complementary sequence of the P2 primer (SEQ ID NO: 1).

6. The method for Columbidae gender identification as claimed in claim 1, wherein the second primer pair comprises the complementary sequence of the SEQ ID NO: 12 and the P2primer (SEQ ID NO: 1), or SEQ ID NO: 12 and the complementary sequence of the P2 primer (SEQ ID NO: 1).

7. The method for Columbidae gender identification as claimed in claim 1, wherein the polymerase chain reaction is a real-time polymerase chain reaction.

8. The method for Columbidae gender identification as claimed in claim 1, wherein the temperature difference between the melting points represented by the two peaks is about 0.5-2.5° C.

9. The method for Columbidae gender identification as claimed in claim 1, wherein the temperature difference between the melting points for the two peaks is about 1.5° C.

10. A method for Columbidae gender identification comprising:
 providing a DNA sample of a bird belonging to the Columbidae family;
 performing a polymerase chain reaction to the DNA sample with a first primer pair of a first primer designed within the region of the SEQ ID NO: 9 or the complementary sequence thereof and a P2 primer (SEQ ID NO: 1) or the complementary sequence thereof, and a second primer pair of a second primer designed within the region of the SEQ ID NO: 10 or the complementary sequence thereof and a P2 primer (SEQ ID NO: 1) or the complementary sequence thereof; and
 determining gender by performing an electrophoresis analysis to a product from the polymerase chain reaction, wherein the result showing two bands indicates a female gender and the result showing one band indicates a male gender.

11. The method for Columbidae gender identification as claimed in claim 10, wherein the Columbidae comprises *Columba livia, Columba pulchricollis* or *Streptopelia tranquebarica*.

12. The method for Columbidae gender identification as claimed in claim 10, wherein the first primer pair comprises the complementary sequence of the SEQ ID NO: 9 and the P2 primer (SEQ ID NO: 1), or SEQ ID NO: 9 and the complementary sequence of the P2 primer (SEQ ID NO: 1).

13. The method for Columbidae gender identification as claimed in claim 10, wherein the second primer pair comprises the complementary sequence of the SEQ ID NO: 10 and the P2 primer (SEQ ID NO: 1), or SEQ ID NO: 10 and the complementary sequence of the P2primer (SEQ ID NO: 1).

14. The method for Columbidae gender identification as claimed in claim 10, wherein the first primer pair comprises the complementary sequence of the SEQ ID NO: 11 and the P2 primer (SEQ ID NO: 1), or SEQ ID NO: 11 and the complementary sequence of the P2 primer (SEQ ID NO: 1).

15. The method for Columbidae gender identification as claimed in claim 10, wherein the second primer pair comprises the complementary sequence of the SEQ ID NO: 12 and the P2 primer (SEQ ID NO: 1), or SEQ ID NO: 12 and the complementary sequence of the P2 primer (SEQ ID NO: 1).

16. The method for Columbidae gender identification as claimed in claim 10, wherein the difference between the nucleotide lengths represented by the two bands is about 148-b.p.

\* \* \* \* \*